United States Patent [19]

Smith

[11] 4,324,922

[45] Apr. 13, 1982

[54] REIMER-TIEMANN ALDEHYDE SYNTHESIS PROCESS

[75] Inventor: William E. Smith, Midland, Mich.

[73] Assignee: The Dow Chemical Company, Midland, Mich.

[21] Appl. No.: 157,727

[22] Filed: Jun. 9, 1980

Related U.S. Application Data

[63] Continuation-in-part of Ser. No. 53,130, Jun. 28, 1979, abandoned.

[51] Int. Cl.³ ............................................. C07C 45/00
[52] U.S. Cl. .................................................... 568/437
[58] Field of Search ........................................ 568/437

[56] References Cited

U.S. PATENT DOCUMENTS 3,365,500  1/1968  Pontz ................................. 568/437

OTHER PUBLICATIONS

Hickinbottom, Reactions of Organic Compounds (1936), 99–100.

Verzele et al., Bull. Soc. Chim. Belg., vol. 65 (1956), 627–629.

*Primary Examiner*—Bernard Helfin
*Attorney, Agent, or Firm*—Douglas N. Deline; Joyce P. Hill

[57] ABSTRACT

Aromatic hydroxyaldehydes, such as o- and p-hydroxybenzaldehyde, are prepared by the reaction of a phenolic compound, chloroform, and an alkali metal hydroxide at a temperature from about 70° to about 105° C. at elevated pressure according to the Reimer-Tiemann reaction. The process improvement results in decreased reaction time.

6 Claims, No Drawings

REIMER-TIEMANN ALDEHYDE SYNTHESIS PROCESS

CROSS-REFERENCE TO RELATED APPLICATION

This application is a continuation-in-part of copending application Ser. No. 53,130, filed June 28, 1979, now abandoned.

BACKGROUND OF THE INVENTION

In 1876 Reimer together with Tiemann was the first to isolate and identify hydroxyaldehydes as the principal reaction products of phenols and chloroform in an alkaline medium. The direct introduction of an aldehyde group into an aromatic nucleus occurred under the Reimer-Tiemann reaction conditions. Using varying molar ratios of alkali to phenol to which a molar excess of chloroform is added with vigorous stirring, at temperatures between 25° C.–70° C., the reaction is allowed to proceed for several hours or even days. The chemistry of the Reimer-Tiemann reaction has been summarized, for example, by Hans Wynberg, *Chemical Reviews*, Vol. 60, 169 (1960), and by Ferguson, *Chemical Reviews*, Vol. 38, 229 (1946). Aldehyde yields are obtained in the following ranges, 35–40 percent o-hydroxybenzaldehyde, 8–12 percent p-hydroxybenzaldehyde, based on chloroform.

SUMMARY OF THE INVENTION

The Reimer-Tiemann aldehyde synthesis reaction time is significantly reduced by the method of this invention. Accordingly, a phenolic compound, chloroform and an alkali metal hydroxide are combined and reacted at elevated temperature and pressure. Utilizing such conditions it has been surprisingly found that greatly shortened reaction times are possible, illustratively from about 15 minutes to about 1 hour. At the same time it has been found that yield and purity of the hydroxy-substituted aromatic aldehyde produced are not significantly adversely affected by the invented process.

DETAILED DESCRIPTION OF THE INVENTION

The Reimer-Tiemann reaction is a well-known reaction which can be represented by the equation

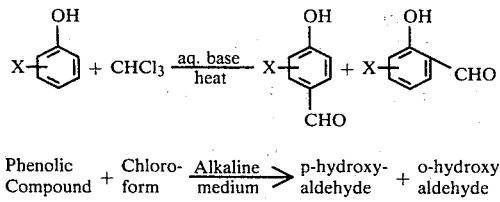

Phenolic Compound + Chloroform $\xrightarrow{\text{Alkaline medium}}$ p-hydroxy-aldehyde + o-hydroxy-aldehyde   I.

wherein X is hydrogen, a hydrocarbon or an inertly-substituted hydrocarbon group. By "inert" is meant inert in the instant process. When X is hydrogen, the phenolic compound is properly called phenol.

The phenols of this invention contain an available activated position usually ortho or para to the hydroxyl group and thus afford a useful means for the preparation of phenolic aldehydes. Suitable phenolic compounds are those phenolic compounds which have been successfully used in the prior art as described in Wynberg, supra, which teaching is herein incorporated by reference. Exemplary classes of phenolic compounds which are suitable for this invention are alkyl phenols, halophenols, hydroxy phenols, alkoxy phenols and the like. The preferred compound is phenol.

The other reactants of this improved process are essentially those which are conventionally used in the Reimer-Tiemann reaction. For example, chloroform is a well-known compound and is commercially available. It is a clear, colorless, volatile liquid having a boiling point of approximately 62° C.

Suitable alkali metal hydroxides are the hydroxides of sodium, potassium or lithium, preferably sodium or potassium hydroxide.

Yields are improved when methanol is added to the chloroform under the conditions reported in U.S. Pat. No. 3,365,500; D. F. Pontz, the teachings of which are incorporated herein by reference.

Many different mole ratios of reactants have been employed successfully in running the Reimer-Tiemann reaction. The use of excess phenol and alkali over the chloroform has been found to give good results, particularly a mole ratio of 2–4 moles of phenol and 3–8 moles of sodium hydroxide per mole of chloroform. However ratios outside these ranges can be used. A variation in the quantity of the phenolic compound, chloroform, alkali metal hydroxide, and water, can be used advantageously to afford flexible ratios of the ortho and para isomers in the aldehyde product. It is also generally desirable to mix the reactants to bring them into better contact during the course of the reaction. Mixing may be accomplished according to any suitable method, for example, magnetic or mechanical stirring, shaking, vibrating or other means of agitation.

The temperature and pressure of the instant process have been found to provide unique benefits in the operation of a Reimer-Tiemann reaction and accordingly comprise the instant invention. Specifically the process is operated at a temperature above the normal boiling point of chloroform.

Additionally, the process is operated at an elevated pressure. By elevated pressure is meant a pressure greater than atmospheric. Suitably, pressures up to about 100 atmospheres may be employed. Preferably, when utilizing the previously mentioned operating temperatures, the necessary pressure may be generated autogenously due to the volatile nature of chloroform and azeotropes thereof formed in the system. Such pressures may be formed for example by combining the reactants and heating in a closed pressure-withstanding reaction vessel to the desired temperature. Additional means of generating elevated pressures, as for example, use of a pressurizing medium such as nitrogen or helium, may also be employed. Suitably, the temperature of the reaction can be from about 70° C. to about 105° C., and preferably from about 80° C. to about 100° C. Operation at lower temperatures can reduce the reaction rate, while operation at higher temperatures can lead to the formation of undesirable resinous by-products.

As previously explained, operation according to the instant invention results in relatively good yields of aldehyde product in as short a reaction time as about one hour or less.

After the reaction is substantially complete, the reaction mixture is cooled and the reaction product recovered by known techniques. The alkali is neutralized and the aldehyde released by the addition of a suitable acid such as a sulfuric acid or hydrochloric acid. The organic layer containing phenol is removed. The o-hydroxyaldehyde is then separated from the less volatile p-hydroxy compound by steam distillation or other suitable means.

This process can be varied and modified in obvious ways to adapt it to various requirements, for example, to permit semi-continuous or continuous operation. The batchwise procedure outlined in the examples below has been found to give good results.

The following examples are given to illustrate the method of this invention; however, the specific details of these examples are not to be taken as limitations upon the invention.

EXAMPLE 1

A solution of 25 grams (0.62 mole) of sodium hydroxide, 100 grams (5.55 moles) of water, 11.9 grams (0.1 mole) of chloroform and 27 grams (0.28 mole) of phenol was added to a pressure reactor equipped with a thermocouple well and having a capacity of 460 milliliters (ml). The thermocouple well was put in place and the cap was screwed on the reactor. The reactor vessel was placed in a rack and shaken. While being continuously shaken, the reactor vessel and contents were heated by gas flame to 80° C.–88° C. and maintained at that temperature for about 12 minutes. The reactor vessel and contents were then cooled with water to 18° C. The cap was unscrewed and the reaction product removed. The recovered products were o-hydroxybenzaldehyde, p-hydroxybenzaldehyde and insoluble tar. Based on the conversion of chloroform in the process, a 52.0 percent yield of combined aldehydes was obtained from the 0.1 mole of chloroform. A standard silver nitrate method, more fully described by J. J. Lingane in *Electroanalytical Chemistry*, Chapter 6, Wiley, N.Y. (1958), was used to analyze for sodium chloride to determine the extent to which the reaction had gone to completion. This analytical technique revealed the presence of 0.28 mole of NaCl. Accordingly, it was determined that the reaction was substantially complete in about 12 minutes.

EXAMPLES 2–8

In substantially the same manner as in Example 1, seven additional runs were made under autogenous pressure with the specified variations in reaction time, reaction temperature and sodium hydroxide concentration. The molar ratio of reactants (sodium hydroxide:chloroform:phenol) was also maintained at 0.62:0.1:0.28 for these experiments. Each run with 20 percent caustic involved the addition of 125.0 grams of the aqueous caustic solution, 27.0 grams of phenol and 11.9 grams of chloroform to the reactor vessel. Each run with 50 percent caustic contained 100 grams of the aqueous caustic solution, 54 grams of phenol and 23.8 grams of chloroform. Since an excess of phenol was used in the reaction, yields are based on conversion of chloroform ($HCCl_3$), which was added in a stoichiometric amount. The conditions and results are recorded in Table I below.

TABLE I

| | Reimer-Tiemann Reaction in a Sealed, Pressure Reactor Vessel | | | | | |
|---|---|---|---|---|---|---|
| | Reaction Conditions | | | Results | | |
| Example No. | Time (minutes) | Temperature °C. | % Concentration of NaOH | % Aldehyde yield Based on $HCCl_3$ | Mole Ratios o-:p-isomer | % Conversion of $HCCl_3$ to Product |
| 2 | 1 | 62 | 20 | 5.5 | 1.2:1 | 15.3 |
| 3 | 10 | 62 | 20 | 25.8 | 1:1 | 48.0 |
| 4 | 12 | 80–88 | 20 | 52.0 | 1:1 | 93.3 |
| 5 | 12 | 70 | 20 | 46.4 | 0.9:1 | 84.0 |
| 6 | 12 | 85–94 | 50 | 43.1 | 1.8:1 | 81.0 |
| 7 | 12 | 100–104 | 50 | 45.5 | 1.7:1 | 90.7 |
| 8 | 20 | 62 | 20 | 31.1 | 1.1:1 | 60.0 |

The above data reveal that operating under the conditions of pressure and temperature of the invention, high conversion of chloroform to end product is rapidly obtained.

What is claimed is:

1. A process for preparing aromatic hydroxyaldehydes comprising reacting by contacting a phenolic compound, chloroform and aqueous alkali metal hydroxide at a temperature from about 70° C. to about 105° C. and at an elevated pressure less than about 100 atmospheres for a time sufficient to form substantial amounts of aromatic hydroxyaldehyde and subsequently recovering the aromatic hydroxyaldehyde formed.

2. The process of claim 1 wherein the phenolic compound is phenol.

3. The process of claim 1 wherein the alkali metal hydroxide is sodium or potassium hydroxide.

4. The process of claim 1 wherein the temperature is from about 80° C. to about 100° C.

5. The process of claim 1 or 4 wherein the pressure is autogenous pressure.

6. The process of claim 1 wherein methanol is additionally present.

* * * * *